United States Patent [19]
Kock et al.

[11] Patent Number: 5,509,406
[45] Date of Patent: Apr. 23, 1996

[54] ANESTHESIA DEVICE

[75] Inventors: Mikael Kock, Akersberga; Georgios Psaros, Tullinge; Göran Skog, Bromma, all of Sweden

[73] Assignee: Siemens Elema AB, Solna, Sweden

[21] Appl. No.: 504,409

[22] Filed: Jul. 20, 1995

[30] Foreign Application Priority Data

Jul. 20, 1994 [SE] Sweden ................................ 9402537

[51] Int. Cl.$^6$ .................................................. A61M 16/01
[52] U.S. Cl. .............................. 128/203.14; 128/200.24; 128/203.12; 128/205.18
[58] Field of Search ........................... 128/203.12, 203.14, 128/203.28, 200.24, 204.21, 205.18, 205.19, 205.13, 205.24

[56] References Cited

U.S. PATENT DOCUMENTS

| | | | |
|---|---|---|---|
| 4,587,967 | 5/1986 | Chu et al. | 128/204.21 |
| 4,932,401 | 6/1990 | Perkins | 128/203.12 |
| 4,957,107 | 9/1990 | Sipin | 128/204.21 |
| 5,049,317 | 9/1991 | Kiske et al. | 261/16 |
| 5,253,640 | 10/1993 | Falb et al. | 128/200.14 |
| 5,265,594 | 11/1993 | Olsson et al. | 128/204.18 |
| 5,398,675 | 3/1995 | Henkin et al. | 128/203.12 |
| 5,400,777 | 3/1995 | Olsson | 128/204.18 |

FOREIGN PATENT DOCUMENTS

| | | |
|---|---|---|
| 2062475 | 5/1981 | United Kingdom. |
| 2226763 | 7/1990 | United Kingdom. |

OTHER PUBLICATIONS

Operating mnaual for Servo Anesthesia Circle 985, Siemens Elema AB, Life–Support Systems Division, pp. 1.6–1.7 (Jul. 1991).

*Primary Examiner*—Edgar S. Burr
*Assistant Examiner*—Eric P. Raciti
*Attorney, Agent, or Firm*—Hill, Steadman & Simpson

[57] ABSTRACT

An anesthesia system has a fresh gas source for supplying a defined flow of fresh respiratory gas to a respiratory circuit wherein the flow is regulated by a flow valve which is controlled on the basis of a flow measured by a flow meter. The anesthesia system is permits the flow meter to be calibrated while the system is in operation to permit the supply of a continuous, or substantially continuous, flow of fresh respiratory gas to the respiratory circuit.

7 Claims, 2 Drawing Sheets

ANESTHESIA DEVICE

BACKGROUND OF THE INVENTION

1. Field of the Invention

The present invention is directed to an anesthesia system of the type having a respiratory circuit which conveys respiratory gas to a patient and having a flow meter which measures a flow of fresh respiratory gas, the flow meter requiring periodic calibration.

2. Description of the Prior Art

An anesthesia system has two basic tasks. One is to anesthetize a patient and keep the patient anesthetized. The other is to maintain the patient's respiration during the time the patient is anesthetized. Normally, a respiratory gas containing nitrous oxide ($N_2O$), oxygen ($O_2$) and an anesthetic gas is supplied to the patient. Swedish Published Application 443 722 corresponding to United Kingdom Application 2,226,763 describes one such anesthesia system. This known anesthesia system has a respiratory circuit in which respiratory gas circulates between the patient and a respiratory gas reservoir. An absorber removes carbon dioxide from gas expired by the patient before the gas is returned to the patient in the next breathing cycle. Since the patient always consumes some gas, oxygen and anesthetic gas in particular, fresh respiratory gas is added to the respiratory circuit from a fresh gas source. Surplus gas in the respiratory circuit is removed via a relief valve.

Fresh gas is supplied to the respiratory circuit via rotameters which at a specific pressure supply a specific flow. In this known anesthesia system, oxygen is supplied via one rotameter and nitrous oxide via another rotameter. The gases are then mixed and pass an anesthetic vaporizer before the final mix of respiratory gas is supplied to the respiratory circuit. Since the rotameters and the anesthetic vaporizer operate at relative low pressures and the gas sources contain highly pressurized gas, pressure regulators are arranged between the rotameters and the gas sources in order to limit the pressure.

In certain of the operating modes of an anesthesia system, a specific pressure is desired at the end of expiration, i.e., a PEEP (Positive End Expiratory Pressure). This pressure is selected by the physician and can be varied during the patient's treatment. One problem which could thereby arise is that the flow of fresh respiratory gas selected by the physician may not always be the actual flow of fresh respiratory gas supplied to the respiratory circuit, since the flow from the rotameters depends on the counterpressure in the respiratory circuit. Another problem arising from the use of manual rotameter systems is that the physician sometimes wishes to supply a specific tidal volume to the patient at each inspiration during anesthesia. The anesthesia system is therefore generally controlled so a specific volume of respiratory gas is released from the respiratory gas reservoir and is imposed on the patient during inspiration. This imposed volume of respiratory gas must be compensated for the flow of fresh respiratory gas which is simultaneously supplied to the respiratory circuit. As previously noted, the selected flow of fresh respiratory gas may not be the same as the flow of fresh respiratory gas actually supplied, a circumstance causing problems in the administration of a specific tidal volume to the patient. Even greater problems can arise when the anesthetist wishes to change the flow of fresh respiratory gas to the respiratory circuit. Every time the flow of fresh respiratory gas is changed, control of the tidal volume from the gas reservoir must be changed to ensure that the correct tidal volume continues to be supplied. This is particularly difficult for the physician, since the flow of fresh respiratory gas is calculated in liters/minute and the tidal volume is calculated in liters/breath. Even if the unit "tidal volume" is replaced with the "minute volume" (tidal volume multiplied by the number of breaths/minute) the patient is to inspire, the calculation is not simplified, in principle, for the physician, since breaths are imposed intermittently, and fresh respiratory gas is supplied continuously.

In conventional ventilator/respirator treatment, very accurate regulation and administration of specific tidal volumes to a patient are well-known. For example, the Servo Ventilator 900 C/D from Siemens-Elema AB, Sweden, can be regulated with high accuracy and can supply a virtually exact flow of gas to a patient. In principle, flow regulation is then based on a servo-controlled feedback system in which a flow meter measures flow and a step motor-regulated scissor valve regulates the actual flow. The flow meters which are employed need some form of periodic calibration. For the Servo Ventilator 900 C/D calibration can easily be made. The ventilator only supplies respiratory gas at the specified flow rate during the inspiratory phase and during the expiratory phase the scissor valve completely blocks the flow of gas. The flow meter can therefore be zeroed during the expiratory phase, when no gas flows past the meter. The valve can then supply a correct flow in the next inspiratory phase. In order to further increase the accuracy of the delivered gas flow, the measurement signal from the flow meter is compensated for the current gas mixture before the control signal to the scissor valve is generated. Compensation for the current gas mixture is performed, since the viscosity of the gas mixture affects the mixture's flow.

In the course of the development of a new anesthesia system by Siemens-Elema AB it was decided to utilize the advantages of the Servo Ventilator 900 C/D with regard to its ability to regulate the supply of an almost exact flow. This also conveyed economic benefits in respect to both development costs and production costs. The result was the Servo Anesthesia Circle 985, described in an Operating Manual, AG 0791 0.5, July 1991. In practice, this anesthesia system utilized a slightly modified Servo Ventilator 900 C/D to regulate the supply of fresh respiratory gas to a respiratory circuit. This resulted in an anesthesia system which, in contrast to the known rotameter anesthesia systems, was capable of supplying a well-defined flow of fresh respiratory gas to the respiratory circuit. This anesthesia system was thus able to achieve a number of advantages, since a very efficient ventilator was employed to control the delivery of fresh respiratory gas. For example, the ability to use the anesthesia system for all known anesthesia modes increased. The Servo Anesthesia Circle 985 can, e.g., be used in a completely open anesthesia system, i.e., all the gas expired by the patient is sent to an evacuation unit, and only fresh respiratory gas is delivered to the patient in each inspiration. Since fresh respiratory gas is only supplied during the inspiratory phase, the tidal volume can be easily set and imposed on the patient, with no need for complex calculations by the physician. The anesthesia system can also be used for different kinds of closed and semi-open respiratory circuits.

The use of a known ventilator as the core of the new anesthesia system also imposed certain limitations, inherent in the ventilator used for the anesthesia system, on the new anesthesia system. For example the anesthesia system could only permit the supply of gas during the inspiratory phase, i.e. the flow valve was completely closed during the expiratory phase to zero the flow meter, so that the almost exact flow could be maintained during the inspiratory phase.

Because of the need to calibrate the flow meter, a continuous flow of fresh respiratory gas could not be supplied to the respiratory circuit with this new anesthesia system. The continuous supply of fresh gas generally only occurs in anesthesia systems employing rotameters. It should be noted, that it does not matter to the patient, as regards the induction or safety of anesthesia, whether fresh respiratory gas is supplied continuously or intermittently. Total gas consumption will actually be lower in an intermittent fresh gas delivery system, if a flow of the same magnitude as in continuous delivery is supplied. With continuous supply, however, the respiratory circuit can be flushed more rapidly (in order to empty the respiratory circuit of anesthetic gas when the patient is to be revived or when some other anesthetic is to be administered).

During subsequent development of other ventilator systems, a unique valve system for the Servo Ventilator 300 was designed within Siemens-Elema AB which is described in U.S. Pat. No. 5,265,594. This new valve system has the ability to control extremely accurate flows in a flow range from a few milliliters a minute up to about ten liters a minute. The newly developed valve system is also capable of controlling continuous flows with no loss of its extremely high accuracy. This new valve system would therefore seem well-suited for use in conjunction with the development of anesthesia systems. The newly developed valve system, however, unfortunately requires a specific minimum input pressure for optimum operation. This minimum pressure is higher than the pressure which occurs in the supply of fresh respiratory gas to the respiratory circuit in the known Servo Ventilator 985 anesthesia system. This valve system could therefore not replace the existing valve system for this purpose.

Since intermittent supply and continuous supply of fresh respiratory gas both convey advantages, achieving an anesthesia system giving physicians a choice between these two types of supply, hitherto unavailable in anesthesia systems, would be desirable. A designer of this very special type of anesthesia system therefore face the problem of trying to achieve an anesthesia system offering the physician a choice in the way in which fresh respiratory gas is supplied to the respiratory circuit, i.e. continuously or intermittently. Delivery must also be as accurate as possible, irrespective of the supply option selected by the physician, As the above shows, achieving this has not been possible by combining any of the known anesthesia systems.

SUMMARY OF THE INVENTION

It is an object of the present invention to provide an anesthesia system which allows a continuous flow of fresh respiratory gas to be supplied to the respiratory circuit. It is a further object of the present invention to provide a ventilator system wherein a valve system of the type described in U.S. Pat. No. 5,265,594 can be employed to provide a wide range of flow control.

It is another object of the present invention to provide an anesthesia system which allows a physician to choose between intermittent supply and continuous supply of fresh respiratory gas.

The above objects are achieved in accordance with the principles of the present invention in an anesthesia system wherein the control device is capable of calibrating the flow meter independently of the inspiratory phase or the expiratory phase and wherein the control device controls the flow valve, even during the expiratory phase, on the basis of the flow of fresh respiratory gas measured by the flow meter.

The realization that calibration of the flow meter is the major obstacle in achieving a continuous flow of fresh respiratory gas has contributed in part to promoting the development of such an anesthesia system. The solution to the described problem was found in the perceptive notion of disassociating the flow meters calibration requirements from its function for measuring fresh respiratory gas to the respiratory circuit. Regulating the flow valve can then be performed even during the expiratory phase. This solution allows the possibility of effective flow meter calibration permitting an essentially continuous flow of fresh respiratory gas to be delivered to the respiratory circuit or permitting flow meter calibration at the same time as a flow of fresh respiratory gas passes the meter.

A substantially continuous flow of fresh respiratory gas is achieved according to the invention in that the control device, regularly at a first interval which is longer than the sum of the duration of the inspiratory phase and the expiratory phase, closes the flow valve for a second interval, which is considerably shorter than the expiratory phase, for zeroing the flow meter.

It is advantageous for the second interval to be less than one-tenth of a second.

It has been noted that it only takes a very brief period of time to zero the flow meter, a procedure which previously occurred during the expiratory phase. A good measurement value and a reliable supply of fresh respiratory gas can therefore be achieved when the flow valve closes for about one-tenth of a second, the flow meter then being zeroed, and then reopens to pass the accurate flow. This can be repeated, e.g., every few breaths. Compensation for the current gas mixtures viscosity is performed in a known manner.

A completely continuous flow of fresh respiratory gas can be supplied to the respiratory circuit with an anesthesia system according to the invention having a fresh gas source with an enclosure whose volume can be varied from a minimum volume to a maximum volume. A filling flow of fresh respiratory gas is supplied to the enclosure during a first time period from a gas source, this filling flow partly filling the enclosure with fresh respiratory gas and partly being conveyed to the respiratory circuit via the fresh gas line. The enclosure is emptied of fresh respiratory gas to the respiratory circuit via the fresh gas line during a second time period in a manner to cause a defined volume of fresh respiratory gas to pass the flow meter during the second time period. The control device includes an integrator which during the second time period, integrates the flow measured by the flow meter in order to obtain a measurement value for the volume of fresh respiratory gas passed. A comparator compares the measurement value for the volume of fresh respiratory gas passed to the defined volume of fresh respiratory gas, and a regulator unit automatically calibrates the flow meter if the measurement value deviates from the defined volume.

Since the volume of fresh respiratory gas passed is known, as well as the duration of its passage, the integrated measurement signal from the flow meter, for the same period of time, should indicate the same volume. Each time the known volume passes the flow meter, the flow meter can be calibrated with increasing accuracy (and be kept accurately calibrated). This can be achieved with no need to interrupt the flow to the respiratory circuit. Ensuring that the pressure in the means is the same at the start and at the end of the second time period, so there is no compression or decompression of respiratory gas in the enclosure, would be additionally desirable. Since a passed volume is employed for calibrating the flow meter, no compensation is required for the gas mixture's viscosity. This compensation is automatically performed when the flow meter is calibrated. This solution also ensures that any leakage in the system is easily detected.

Since the enclosure contains a known volume at a known pressure, the emptying time can be calculated from the minute volume set for fresh gas delivery. Leakage is present if the actual emptying time becomes too short or if the filling time becomes too long.

Preferably, the enclosure is a bellows which is moveable between a first limit position, corresponding to the maximum volume, and a second limit position, corresponding to the minimum volume. A first position sensor is arranged to detect when the bellows is at a defined distance from its first limit position, thereupon generating a first position signal and supplying it to the control device, and a second position sensor is arranged to detect when the bellows is at a defined distance from its second limit position, thereupon generating a second position signal and supplying it to the control device. The defined volume corresponds to the change in volume of the bellows when moving between the first sensor and the second sensor and the second time period corresponds to the time elapsing from generation of the first position signal to the generation of the second position signal when the bellows is emptied.

As a result of the relationship between pressure and flow, maintaining a constant pressure in the bellows is desirable, as noted above, at least at the beginning and end of the second time period. Regulating pressure in the bellows to keep it constant during both filling and emptying of the bellows would then be advantageous. This would facilitate regulation of an exact flow with servo-controlled feedback regulation. Maintaining exact pressure is difficult, however, when the bellows is at one of its limit positions. Minor variations in the pressure of the respiratory gas can then occur in the bellows. For the best possible calibration, the first position sensor and the second position sensor are therefore respectfully placed at a defined distances from the limit positions. The defined volume is accordingly measured during the period of time in which constant pressure can reliably be maintained in the bellows, and both measurement and calibration can therefore be performed more accurately.

In a further embodiment of the anesthesia system according to the invention, the respiratory circuit is a recirculating respiratory circuit, in which at least some of the respiratory gas expired by the patient is fed back to the patient after the removal of carbon dioxide. The recirculation respiratory circuit includes a respiratory gas reservoir with an adjustable volume which decreases during inspiration, when respiratory gas is carried from the respiratory gas reservoir to the patient, and increases during expiration, when respiratory gas is conveyed from the patient to the respiratory gas reservoir. The recirculating respiratory circuit also includes a drive unit connected to the respiratory gas reservoir in order to regulate the reservoir's volume, and the control device is connected to the drive unit to control the drive unit on the basis of the measured flow of fresh respiratory gas in the fresh gas line and an adjustable tidal volume, so the desired tidal volume is supplied to the patient in each inspiratory phase.

This design for the anesthesia system achieves completely automatic control of the tidal volume. This is not possible with anesthesia systems employing rotameters. The physician no longer has to make any calculations of the volume to be supplied from the respiratory gas reservoir to the patient so a desired tidal volume is achieved with a view to the flow of fresh respiratory gas. This is automatically performed by the anesthesia system according to the invention. Changes in the flow of fresh respiratory gas in the anesthesia system according to the invention cause the volume of gas from the respiratory gas reservoir to be adapted to these changes in the flow of fresh respiratory gas. In principle, this also means that the anesthesia system can be easily switched between open and different forms of closed or semi-closed operating modes. If, for example, the physician sets a sufficiently fast flow of fresh respiratory gas, the system operates as an open system. If the physician elects to supply small, intermittent doses of fresh respiratory gas to compensate for gas losses in the respiratory circuit, the most closed system possible would result.

It is advantageous for the fresh gas line to be formed at least in part by a soft, deformable tube and for the flow valve to be a step motor-regulated scissor valve, arranged on the deformable tube, to regulate the flow of fresh respiratory gas in the fresh gas line by radially compressing the tube.

In general, one such flow valve is known from the aforementioned Servo Ventilator 900 C/D.

DESCRIPTION OF THE PREFERRED EMBODIMENTS

Figure 1:
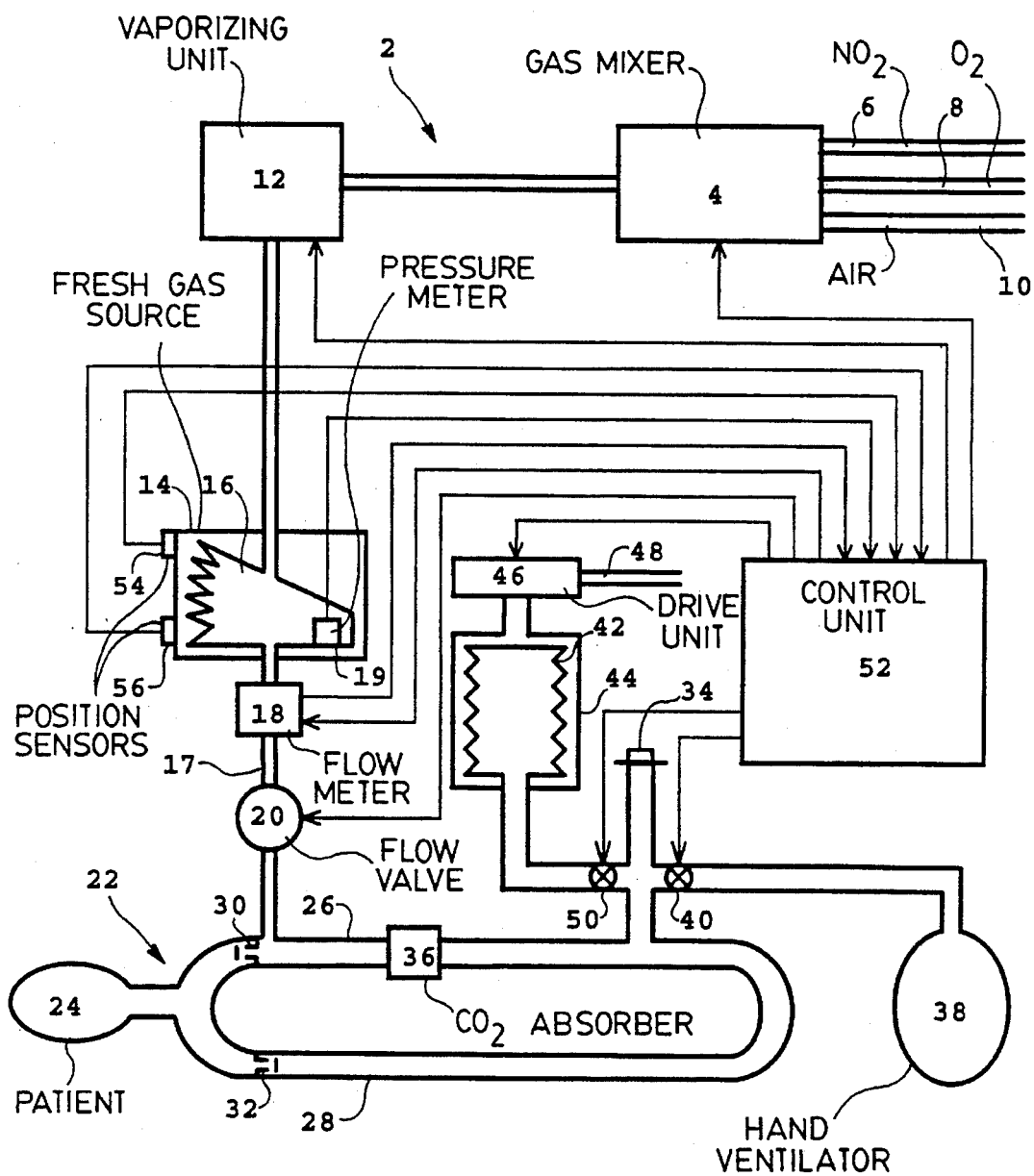
FIG. 1 is a schematic illustration of an anesthesia system constructed in accordance with the principles of the present invention.

An inventive anesthesia system 2 is shown in FIG. 1. The anesthesia system 2 includes a gas mixer 4, which can be supplied with nitrous oxide via a nitrous oxide connector 6, oxygen via an oxygen connector 8 and air via an air connector 10. During anesthesia, the patient is generally given only a mixture of nitrous oxide and oxygen, plus some anesthetic gas, however, a mixture of air and oxygen can be supplied to the patient when the patient is revived. Nitrous oxide and oxygen in defined proportions are usually mixed in the gas mixer 4, and the mixed gas is sent to the vaporizer unit 12. An anesthetic can be vaporized in the vaporizer unit 12 and added to the gas mixture from the gas mixer 4 before it is conveyed as fresh respiratory gas to a fresh gas source 14. A first bellows 16 is arranged in the fresh gas source 14. Fresh respiratory gas can then be conveyed from the first bellows 16 in the fresh gas source 14, through a fresh gas line 17, a 5 flow meter 18 and a flow valve 20, to a respiratory circuit 22. The flow valve 20 regulates the flow of fresh respiratory gas to the respiratory circuit 22 on the basis of the flow (possibly compensated for the viscosity of the current gas) measured by the flow meter 18. In order to obtain the most exact possible value for the flow, the pressure of the fresh respiratory gas in the first bellows 16 is regulated to keep it constant. A pressure meter 19 is arranged to measure pressure in the first bellows 16. During a first time period, fresh respiratory gas, at the constant pressure, is supplied from the gas mixer 4, via the vaporizer unit 12, to the first bellows 16 in order to fill same. Flow from the gas mixer 4 is blocked during a second time period, and the first bellows 16 is emptied by being compressed while the constant pressure is maintained.

The respiratory circuit 22 is connected to a patient 24. Fresh respiratory gas from the fresh gas source 14 is fed into an inspiratory line 26 which conveys respiratory gas to the patient 24. Expired respiratory gas is conveyed from the patient through an expiratory line 28. The direction of respiratory gas flow in the respiratory circuit 22 is controlled by a first check valve 30, located in the inspiratory line 26, and a second check valve 32, located in the expiratory line 28.

The anesthesia system 2 can operate according to a number of different principles. It can, e.g., operate as an open anesthesia system, only fresh respiratory gas from the fresh gas source 14 then being supplied to the patient 24 in each breath. Expired gas is then carried through an outlet valve 34 to an evacuation unit or the like (not shown in the figure).

The anesthesia system 2 can also operate with some form of 5 respiratory gas recirculation. This means that at least part of the respiratory gas expired by the patient 24 is fed back to the patient in the next breath. For this purpose, the respiratory gas passes through a carbon dioxide absorber 36. The breathing rhythm and depth of breathing of the patient 24 can be controlled in two different ways. The physician can manually control the breathing of the patient 24 with a hand ventilator 38 which can be connected to the inspiratory line 26 via a first switching valve 40. When the physician squeezes the hand ventilator 38, he or she forces the patient 24 to inhale respiratory gas from the hand ventilator 38, and when the physician relaxes pressure on the hand ventilator 38, her or she allows the patient 24 to exhale.

The breathing of the patient 24 can also be controlled mechanically. For this purpose, a second bellows 42, located in a container 44, is connected to the inspiratory line 26. Control is performed using a second switching valve 50. Mechanical compression of the second bellows 42 imposes an inhalation on the patient 24. The patient 24 is able to exhale when pressure on the second bellows 42 is mechanically relaxed. Regulation of the position of the bellows 42 ensues by means of a drive unit 46 which, by supplying and removing compressed air to and from the space between the second bellows 42 and the walls of the container 44, changes the position of the second bellows 42 inside the container 44. The drive unit 46 has a compressed air connector 48 for admitting the compressed air used to regulate the position of the second bellows 42. The compressed air line 48 can be shared with the air connection 10 to the gas mixer 4.

The anesthesia system 2 is controlled and regulated by a control unit 52. The control unit 52 is therefore connected to the gas mixer 4 to regulate the composition of the respiratory gas and the flow of mixed respiratory gas to the fresh gas source 14, to the vaporizer unit 12 to regulate the vaporization of anesthetic, to the drive unit 46 to regulate the breathing cycles of the patient 24 in mechanical ventilation, to the switching valves 40 and 50 to connect/shut off the hand ventilator 38 and second bellows 42 respectively from the respiratory circuit 22, to the flow valve 20 to regulate the flow of fresh respiratory gas, and to the flow meter 18 for calibrating same.

The flow meter 18 must be periodically calibrated. In principle, this can be performed if the control device 52 closes the flow valve 20 for a brief period of time, e.g. one or a few tenths of a second, and then zeroes the flow meter 18. This can be carried out at regular intervals, i.e., from several times a minute to several times an hour. The control device 52 is then able to regulate the supply of fresh respiratory gas from the first bellows 16 to the respiratory circuit 22 according to different gas supply options. For example, fresh respiratory gas can be supplied only during inspiratory phases, only during expiratory phases or continuously (except during the brief interval) during both inspiratory phases and expiratory phases. When the flow meter 18 is zeroed in this way, the measurement signal should be compensated for the gas mixture's viscosity before the control signal is generated for the flow valve 20.

Another way of calibrating the flow meter 18 is shown in FIG. 1. The first bellows 16 has a given physical volume which can also be set for different levels. Since pressure in the first bellows 16 is regulated to keep it constant, the volume of gas in the first bellows 16, when the bellows is filled to a defined level, is also known. A first position sensor 54 is arranged to detect when the first bellows 16 approaches its upper position, i.e. when it is virtually full, and a second position sensor 56 is arranged to detect when the first bellows 16 approaches its lower position, i.e., when it is virtually empty. The fresh gas unit 14 operates in such a way that when the first bellows 16 is empty, it fills with a flow of respiratory gas from the gas mixer 4, via the vaporizer unit 12, at constant pressure. The flow from the gas mixer 4 is then sufficient to fill the first bellows 16 and to produce a flow of respiratory gas to the respiratory circuit 22. When the first bellows 16 is full, the flow from the gas mixer 4 is cut off, and gas in the first bellows 16 is sent to the respiratory circuit 22 when the first bellows 16 is compressed. During the emptying of the first bellows 16, an exact, known volume of fresh respiratory gas therefore passes through the flow meter 18. When the time it takes to empty the first bellows 16 is known, calibration of the flow meter 18 becomes possible even while a flow of respiratory gas is passing therethrough. In this calibration procedure, the viscosity of gas mixture is automatically taken into account, and no separate compensation is necessary.

Figure 2:
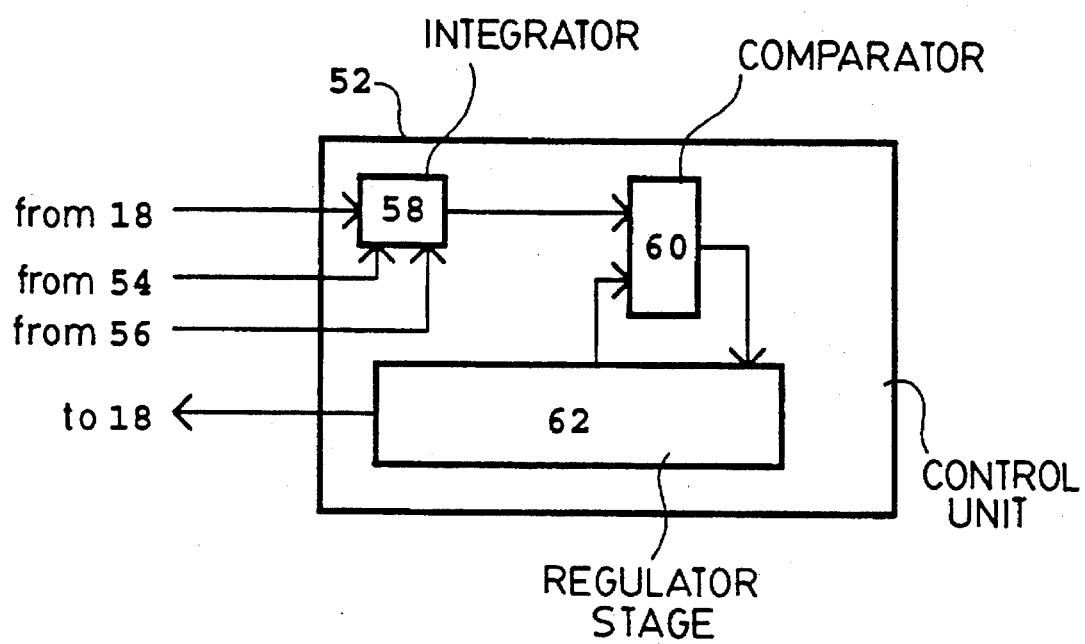
FIG. 2 is a block diagram of an exemplary embodiment of the control unit used in the anesthesia system of FIG. 1.

FIG. 2 shows how the known volume and the emptying time can be utilized for calibrating the flow meter 18. The figure only shows the functional units required for calibration. The first position sensor 54 is arranged to sense when the filled first bellows 16, under compression, passes a defined position. The first position sensor 54 then emits a signal which activates an integrator 58. The integrator 58 uses the measurement signal from the flow meter 18 as an input signal. When the first bellows 16 approaches its second end position, i.e. when it is virtually empty, this is registered by the second position sensor 56 which then emits a signal which stops integration of the measurement signal from the flow meter 18. The integrated measurement signal then corresponds to the measured volume of fresh respiratory gas which has passed the flow meter 18. This volume signal is sent to a comparator 60 in which it is compared to the actual volume of the first bellows 16 between the two positions registered by the first position sensor 54 and the second position sensor 56. The difference between the volume determined in the integrator 58 and the actual volume is sent to a regulator stage 62 which calculates, when necessary, a requisite calibration of the flow meter 18 and accordingly sends a calibration signal to the flow meter 18. With this calibration system, a continuous flow of fresh respiratory gas can therefore be supplied to the respiratory circuit 22.

The signal processing involved in utilizing the signals from the first position sensor 54 and the second position sensor 56 for determining the integration interval can also be performed in other ways. For example, the time from which the first bellows 16 passes the first position sensor 54 until it passes the second position sensor 56 can be measured by a timer. The measured time is then the integration interval.

The measured time can also be used for determining an average value for flow on the basis of the known actual volume which is then compared to an average value for the flow measured by the flow meter 18. The difference between the measured average value and the calculated average value for the flow of fresh respiratory gas can then be utilized for calculating an appropriate calibration. The described functions can be performed with both hardware and software.

Since the first bellows 16 contains a defined volume and this 30 volume is periodically filled and emptied, any leakage in the fresh gas system can be easily detected. The desired minute volume of fresh respiratory gas to be sent to the respiratory circuit 22 is set by the physician and a signal corresponding to the set minute volume sent to the control unit 52. Both the filling time and the emptying time can be calculated and monitored by the control unit 52. If the filling time becomes abnormally long or the emptying time abnormally short, there is probably a leak in the first bellows 16. An alarm can then be generated to alert personnel to the fault. Moreover, if the second kind of calibration, i.e., with brief closure of the flow valve 20 followed by zeroing of the flow meter 18, was undertaken it may be appropriate to repeat the calibration, because the passing volume is no longer known as a result of the leakage.

Although modifications and changes may be suggested by those skilled in the art, it is the intention of the inventors to embody within the patent warranted hereon all changes and modifications as reasonably and properly come within the scope of their contribution to the art.

We claim as our invention:

1. An anesthesia system comprising:

a respiratory circuit connectable to a patient which delivers a respiratory gas to the patient during an inspiratory phase and which conveys expired respiratory gas from the patient during an expiratory phase;

a fresh gas source containing fresh respiratory gas;

a fresh gas line connecting said fresh gas source to said respiratory circuit;

a flow meter disposed in said fresh gas line which measures a flow of fresh respiratory gas being supplied to said respiratory circuit from said fresh gas source, said flow meter requiring periodic calibration;

a flow valve disposed in said fresh gas line which regulates the flow of fresh respiratory gas therein; and control means connected to the flow meter and the flow valve for operating said flow valve dependent on a measured flow of fresh respiratory gas measured by said flow meter for delivering a defined flow of fresh respiratory gas to the respiratory circuit and for calibrating the flow meter independently of the inspiratory phase and the expiratory phase for maintaining substantially continuous control of said flow valve.

2. An anesthesia system as claimed in claim 1 wherein said control means comprises means for regularly closing, at a first interval which is longer than a sum of the duration of the inspiratory phase and the expiratory phase, said flow valve for a second interval which is substantially shorter than said expiratory phase, for zeroing said flow meter.

3. An anesthesia system as claimed in claim 2 wherein said control means comprises means for closing said flow valve for a second interval which is less than one-tenth of a second.

4. An anesthesia system as claimed in claim 1 wherein said fresh gas source comprises an enclosure having a variable volume variable between a minimum volume and a maximum volume, means for filling said variable volume with a filling flow of fresh respiratory gas during a first time period, said filling flow being divided for filling said variable volume and for supplying fresh respiratory gas to said respiratory circuit via said fresh gas line, means for emptying said variable volume of fresh respiratory gas into said respiratory circuit via said fresh gas line during a second time period with a predetermined volume of fresh respiratory gas passing said flow meter during said second time period, and wherein said control means comprises an integrator for integrating the flow, during said second time period, measured by the flow meter for generating a measurement value for the volume of fresh respiratory gas passed by said flow meter, a comparator which compares said measurement value to said predetermined volume, and regulator means for automatically calibrating said flow meter if said measurement value deviates from said predetermined volume.

5. An anesthesia system as claimed in claim 4 wherein said variable volume comprises a bellows movable between a first position corresponding to said maximum volume and a second position corresponding to said minimum volume, and wherein said control means includes a first position sensor disposed for detecting when said bellows is at a predetermined distance from said first position and for generating a first position signal when said bellows reaches said predetermined distance from said first position, a second position sensor disposed to detect when said bellows is at a predetermined distance from said second position and for generating a second position signal when said bellows reaches said defined distance from said second position, means for calculating said predetermined volume by identifying a change in volume of said bellows dependent on a time elapsing between the generation of said first position signal and said second position signal as said bellows is emptied of fresh respiratory gas.

6. An anesthesia system as claimed in claim 1 wherein said respiratory circuit comprises a recirculating respiratory circuit including a carbon dioxide absorber through which expired respiratory gas is conveyed before recirculation to said patient, a respiratory gas reservoir having an adjustable volume which decreases during inspiration as respiratory gas is conveyed from said respiratory gas reservoir to the patient and which increases during expiration when expired respiratory gas is conveyed from the patient to the respiratory gas reservoir, a drive unit connected to the respiratory gas reservoir for regulating the volume of said respiratory gas reservoir, and said control means comprising means, connected to said drive unit, for operating said drive unit dependent on the flow of fresh respiratory gas measured by said flow meter in said fresh gas line and on a selectable title volume, for supplying a selected title volume to said patient in each inspiratory phase.

7. An anesthesia system as claimed in claim 1 wherein said fresh gas line comprises a deformable tube and wherein said flow valve comprises a scissor valve operated by a stepping motor and disposed for acting on said deformable tube to regulate the flow of fresh respiratory gas through said deformable tube by radially compressing said deformable tube.

* * * * *